(12) United States Patent
He et al.

(10) Patent No.: US 9,588,029 B2
(45) Date of Patent: Mar. 7, 2017

(54) DYNAMICS PERFORMANCE TESTING SYSTEM

(75) Inventors: Manchao He, Beijing (CN); Zhibiao Guo, Beijing (CN); Guofeng Zhang, Beijing (CN)

(73) Assignee: China University of Mining & Technology (Beijing), Beijing (CN)

( * ) Notice: Subject to any disclaimer, the term of this patent is extended or adjusted under 35 U.S.C. 154(b) by 345 days.

(21) Appl. No.: 14/389,193

(22) PCT Filed: Mar. 31, 2012

(86) PCT No.: PCT/CN2012/073417
§ 371 (c)(1),
(2), (4) Date: Sep. 29, 2014

(87) PCT Pub. No.: WO2013/143145
PCT Pub. Date: Oct. 3, 2013

(65) Prior Publication Data
US 2015/0114084 A1    Apr. 30, 2015

(51) Int. Cl.
*G01N 3/303* (2006.01)
*G01M 7/08* (2006.01)
(Continued)

(52) U.S. Cl.
CPC .............. *G01N 3/303* (2013.01); *G01L 1/16* (2013.01); *G01L 5/0052* (2013.01); *G01M 7/08* (2013.01);
(Continued)

(58) Field of Classification Search
CPC ........................................ G01N 3/303
See application file for complete search history.

(56) References Cited

U.S. PATENT DOCUMENTS

| 3,196,671 A | 7/1965 | Dannis |
| 4,405,020 A | 9/1983 | Rassieur |
| 2004/0261494 A1 | 12/2004 | Lee |

FOREIGN PATENT DOCUMENTS

| CN | 2480829 Y | 3/2002 |
| CN | 2311765 Y | 12/2004 |

(Continued)

OTHER PUBLICATIONS

UIAA Dynamic Rope Drop Testing Results with Loads Greater than 80 kg. http://itrsonline.org/wordpress/wp-content/uploads/2014/09/Weber-Hudson1999_ITRSPaper.pdf.*

(Continued)

*Primary Examiner* — Clayton E Laballe
*Assistant Examiner* — Dennis Hancock
(74) *Attorney, Agent, or Firm* — Yunling Ren (57) ABSTRACT

A dynamics performance testing system, for use in testing the dynamics performance of an anchor rod or an anchor rode, comprising a main machine and a measurement and control system. The main machine comprises a vertical machine frame (1), a clamping apparatus (3) arranged on the top of the vertical machine frame (1) and used for vertically clamping the top end of a sample (6), where the sample (6) is provided at the bottom end thereof with a tray (61), a drop-hammering apparatus (2) used for being dropped vertically from the vertical machine frame (1) at a set height to impact the tray (61), a lifting apparatus used for lifting the drop-hammering apparatus at the bottom of the vertical machine frame (1) to the set height, and a protection apparatus used for physical protection and isolation to reduce bodily injury and noise. The measurement and control system controls the drop-hammering apparatus to select a parameter for drop-hammering and a process of lifting and dropping. The real-time impact on the tray (61) when the drop-hammering apparatus is dropped vertically is sensed by (Continued)

a force sensor, while real-time impact data received from a sensor device is analyzed, and a test result is outputted. The dynamics performance testing system is provided with versatility while the test result is accurate and reliable.

16 Claims, 10 Drawing Sheets

(51) Int. Cl.
  *G01L 1/16* (2006.01)
  *G01L 5/00* (2006.01)
(52) U.S. Cl.
  CPC .................. *G01N 2203/028* (2013.01); *G01N 2291/02827* (2013.01)

(56) References Cited

FOREIGN PATENT DOCUMENTS

| CN | 101387569 A | 3/2009 |
|---|---|---|
| CN | 101571515 A | 11/2009 |
| CN | 101581646 A | 11/2009 |
| CN | 101769838 A | 7/2010 |
| CN | 101858225 A | 10/2010 |
| CN | 201635754 U | 11/2010 |
| CN | 102279135 A | 12/2011 |
| CN | 102323152 A | 1/2012 |
| CN | 202101909 U | 1/2012 |
| CN | 102621013 A | 8/2012 |
| JP | 62027546 | 9/1988 |
| JP | 11248611 | 9/1999 |
| JP | 2002174574 | 6/2002 |
| JP | 2004004032 | 1/2004 |
| JP | 2008121304 | 5/2008 |
| JP | 2010076557 | 4/2010 |
| JP | 2010181318 | 8/2010 |
| JP | 2011106544 | 6/2011 |

OTHER PUBLICATIONS

Comparative Testing of High Strength Cord. http://caves.org/section/vertical/nh/49/cthsc/cthsc.html.*
International Search Report of Application No. PCT/CN2012/073423, mailed Jan. 10, 2013.
Article of sharp edge testing of mountaineering ropes 6 conclusions 18.
Office Action issued Sep. 8, 2015 by the JP Office.
EESR issued Nov. 9, 2015 by the EP Office.

* cited by examiner

DYNAMICS PERFORMANCE TESTING SYSTEM

CROSS-REFERENCE TO RELATED PATENT APPLICATIONS

This is a national stage application of PCT/CN2012/073417, filed on Mar. 31, 2012 under 35 U.S.C. 371, which is incorporated reference in its entirety.

TECHNICAL FIELD

The present disclosure relates to a dynamics performance testing system, in particular to a dynamics performance testing system for testing the dynamics performances of constant-resistance and large-deformation anchor rods (ropes) and other common anchor rods (ropes) indoor.

BACKGROUND

In recent years, as the rapid development of the national economy, there is increasing demand for energy in various industries. Surface mines in China are now entering a stage of deep mining one after the other. The problems such as a large quantity of slopes, active faults and the stability of surrounding rocks in chambers are involved in the fields of mining, water conservancy, transportation and the like.

At present, China is in a period of rapid development of various engineering constructions. In the process of mineral exploitation and underground engineering construction, there have been many disasters, such as rock burst, pressure bump, collapse and the like. The control of natural disasters and engineering disasters in the case of high and steep slopes and stable surrounding rocks of roadways mainly relies on the traditional prestressed anchor rod (rope) reinforcement system and derivative supporting structure engineering thereof. However, since the instability of rock mass reinforcing structures is mostly caused by the large deformation of elastic-plasticity, the supporting and reinforcing concept based on the traditional prestressed anchor rod (rope) system has been unable to adapt to the large-deformation development law of rock masses (slope rock masses and tunnel surrounding rocks), and hence the fracture of partial end portions of anchor rods, the fracture of central portions of anchor ropes (rods), repeated repair of supporting areas, twisting, damage and failure of steel frames and other accidents will occur in the roadway supporting process.

To these problems, Professor Manchao HE puts forward the design concept of constant-resistance resisting and deformation absorbing of energy under the enlightenment of the philosophical thought of conquering the unyielding with the yielding and tampering force with mercy, and researches and develops a new anchor rod, i.e. a new constant-resistance and large-deformation anchor rod (e.g., a constant-resistance and large-deformation anchor rod disclosed in the Chinese invention patent publication No. CN101858225A). Moreover, on the basis thereof, a whole set of control concept and technical equipment system with slope reinforcement, slope slide and earthquake disaster monitoring and early warning, and underground engineering support is formed and provides a good exploration mode for solving the problem of large deformation in geotechnical engineering.

After the research and development of the constant-resistance and large-deformation anchor rod (rope), a dynamics performance testing system is required for better performing system test and research on the dynamics performances of the constant-resistance and large-deformation anchor rod (rope), examination of the performances of the constant-resistance and large-deformation anchor rod in resisting and absorbing impact energy, and measurement of the elongation and the radial deformation of a rod body after impact each time. Moreover, the dynamics performance testing system summarizes dynamic-load test data of the constant-resistance and large-deformation anchor rod, generized the variation laws of the elongation, the impact resistance and the impact energy of a constant-resistance machine by the contrastive analysis of test curves, optimizes geometrical parameters and structural parameters of the constant-resistance machine according to the test result, and further improves the ability of the constant-resistance and large-deformation anchor rod in impact resistance. Furthermore, better support is provided for large deformation of soft strata, large deformation of bump (rock burst), large deformation of outburst, large deformation of slope slide, large deformation of seismogenic faults and the like by calculation and relevant measurements.

SUMMARY

The present invention aims to overcome the defects in the related art, and provide a dynamics performance testing system capable of accurately and effectively testing the performances of an anchor rod or an anchor rope in resisting and absorbing impact energy.

The present disclosure adopts the technical proposal that: the present disclosure relates to a dynamics performance testing system, for use in testing the dynamics performances of an anchor rod or an anchor rope, wherein the dynamics performance testing system comprises a main frame and a measure and control system. The main frame includes a vertical frame; a clamping means disposed on the top of the vertical frame and configured to vertically clamp the top of a sample including a sample body and a tray at the bottom of the sample body; a drop hammer device configured to fall vertically from a predetermined height of the vertical frame to impact the tray; a lifting means configured to lift the drop hammer device at the bottom of the vertical frame to the predetermined height; and a protective device for physical protection and isolation to reduce hazards on the human body and the noise. The measure and control device is configured to control parameter selection and the lifting and falling of the drop hammer device in the drop hammer test process, sense real-time impact data to the tray through a force sensor when the drop hammer device falls vertically, analyze the real-time impact data received from a sensing means, and output a test result.

The dynamics performance testing system provided by the present disclosure has at least one of the advantages that: by adoption of the dynamics performance testing system provided by the present disclosure, the dynamics parameters of various anchor rods and anchor ropes, including constant-resistance and large-deformation anchor rods, can be accurately and reliably obtained; the performances of an anchor rod (rope) to be tested in resisting and absorbing impact energy are examined; the elongation and the radial deformation of a rod body after impact each time are measured; and an "impact height-impact deformation" test curve, an "impact height-accumulated deformation" test curve, an "accumulative impact energy-accumulative impact deformation" test curve and an "impact energy-impact resistance" test curve are respectively drawn. Moreover, the variation law of the elongation, the impact resistance and the impact energy of a constant-resistance machine is generized by the contrastive analysis of the test curves; the geometrical parameters and the structural parameters of the constant-resistance machine are optimized according to the test result; the ability of the constant-resistance and large-deformation anchor rod in impact resistance is further improved; the structural parameters and the technical parameters of the constant-resistance and large-deformation anchor rod are further optimized and adjusted; and a better support is provided for large deformation of soft strata, large deformation of bump (rock burst), large deformation of outburst, large deformation of slope slide, large deformation of seismogenic faults and the like.

Moreover, the dynamics performance testing system provided by the present disclosure can test dynamics performances of the anchor rod (rope) by various ways with adoption of control means of different heights or the combination of different heights, and has at least one of the advantages of energy saving, environmental protection and high safety.

DETAILED DESCRIPTION

Detailed description will be given below to the preferred embodiments embodying the characteristics and advantages of the present disclosure. It should be understood that various variations may be made to different embodiments of the present disclosure without departing from the scope of the present disclosure, and the description and the drawings therein are only for illustration in essence and not intended to limit the present disclosure.

The dynamics performance testing system provided by an embodiment of the present disclosure may comprise two parts, namely a main frame and a measure and control system. The main frame may include five parts, namely a vertical frame 1, a drop hammer device 2, a clamping device 3, a lifting device, and a protective device. The measure and control system may include five modules in view of functions, namely a sensing module, a control module, an analysis module, an output module, and a protective module. The above parts will be described below respectively.

1. Vertical Frame

Figure 1:
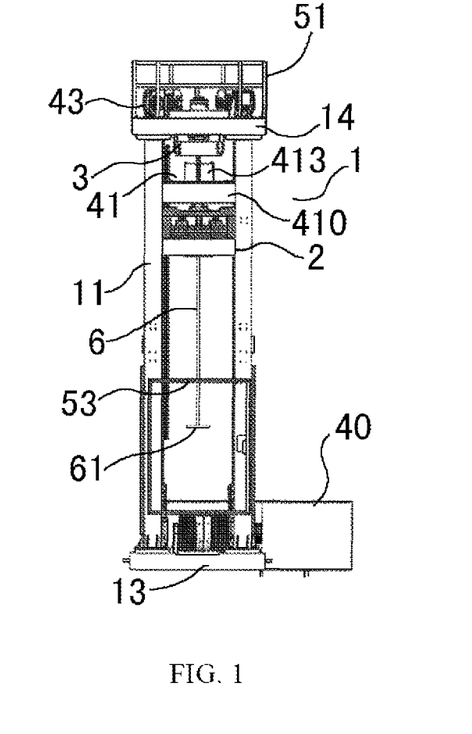
FIG. 1 is a schematic front view of a main machine of a dynamics performance testing system provided by an embodiment of the present disclosure.
Figure 2:
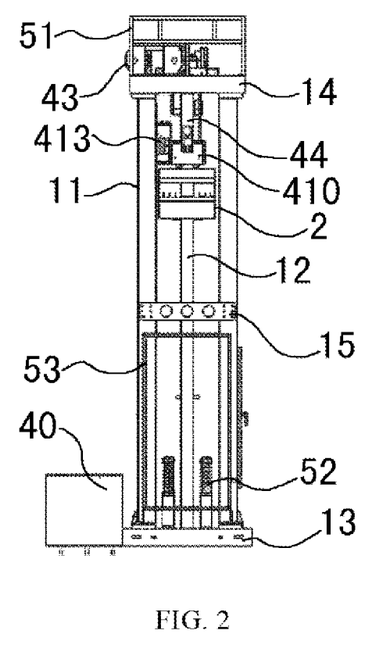
FIG. 2 is a schematic left view of the main machine of a dynamics performance testing system provided by an embodiment of the present disclosure.

As shown in FIGS. 1 and 2, the vertical frame 1 is a vertically arranged frame structure and mainly includes four support columns 11, two guide columns 12, a console 13 and a fixed beam 14. The console 13 is disposed at a bottommost end of the vertical frame 1. Both the support columns 11 and the guide columns 12 are disposed on the console 13. The fixed beam 14 is disposed on the top of the support columns 11 and the guide columns 12. A top platform having a frame structure and being provided with a fence 51 is formed at the position of the fixed beam 14 and configured to place a pulley block 43 of the lifting device and fix the clamping device 3.

As shown in FIGS. 1 and 2, two support columns 11 on each side are connected to each other through a transverse draw plate 15. Both upper surfaces and lower surfaces of the four support columns 11 are fastened on the fixed beam 14 and the console 13 by high-strength hexagon head bolts and butterfly lock washers, so that the vertical frame 1 is guaranteed to have sufficient rigidity. The guide column 12 is configured to guide free-falling of the drop hammer device 2 and is preferably symmetrically disposed at a position of a mid-point between the two support columns 11 on each side.

The guide columns 12 may be lubricated. For this, an appropriate amount of lubricating oil may be regularly applied to the guide columns 12 during lubrication.

As described above, the frame structure of the vertical frame 1 in the present disclosure has at least one of the advantages of reasonable structure, high rigidity, attractive appearance and the like.

2. Drop Hammer Device

As shown in FIGS. 1, 2, 4 and 7, the drop hammer device 2 is configured to fall vertically from a predetermined height of the vertical frame 1 to impact a tray 61 of a sample 6.

The drop hammer device 2 includes main parts such as an upper hammer block 201, a connecting hammer block 202, a lower hammer block 203, a counterweight 23 and a lower hoisting ring 21, and other parts such as a positioning rod 25, a positioning column 281 and 282, a positioning block 24 and a compression nut 242, etc.

The upper hammer block 201 and the lower hammer block 203 are connected to each other through both of the left and right connecting hammer blocks 202 by means of, for instance, bolts 291. A space between the two connecting hammer blocks 202 is configured to place the counterweights 23. A horizontal position among a plurality of groups of counterweights 23 is performed by the positioning rod 25 and the positioning columns 281 and 282.

Figure 8:
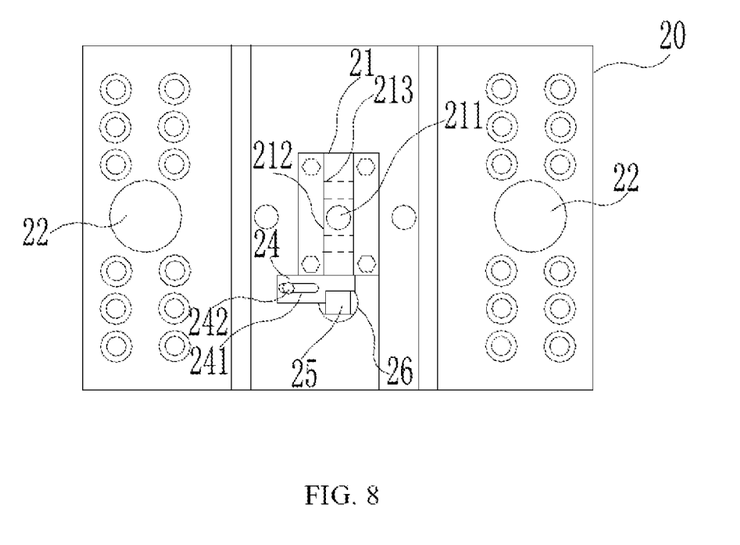
FIG. 8 is a schematic top view of a drop hammer device of a dynamics performance testing system provided by an embodiment of the present disclosure.
Figure 9:
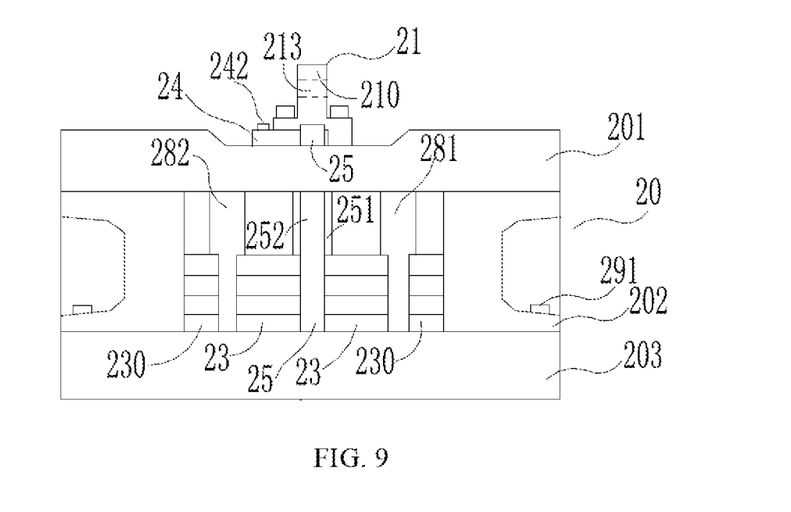
FIG. 9 is a schematic front view of the drop hammer device of a dynamics performance testing system provided by an embodiment of the present disclosure.

As shown in FIGS. 8 and 9, the bottom of the positioning rod 25 is rotatably disposed on an upper surface of the lower hammer block 203. The top of the positioning rod 25 may be in the shape of a right square prism, passes through the upper hammer block 201, and abuts against an orthogonal recessed surface of the positioning block 24 so as to limit the rotation of the positioning rod 25. The positioning block 24 abuts against an end surface 210 of the lower hoisting ring 21 and is provided with a slotted hole 241. The compression nut 242 passes through the slotted hole 241, so as to fix the positioning block 242 onto an upper surface of the upper hammer block 201 and hence limit the rotation of the positioning rod 25, thus the horizontal position of the counterweights can be achieved.

Figure 10:
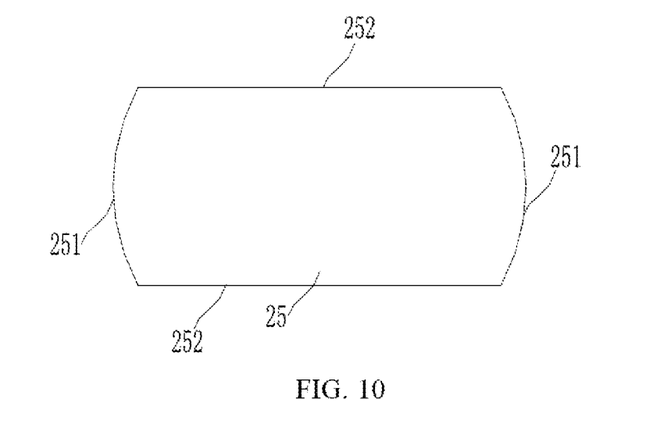
FIG. 10 is a schematic cross-sectional view of a positioning rod in a drop hammer device.

As shown in FIGS. 9 and 10, the positioning rod 25 between the upper hammer block 201 and the lower hammer block 203 has two parallel side surfaces 252 and two circular end surfaces 251. The counterweights 23 are correspondingly provided with circular recesses engaged with the circular end surfaces 251. The radian of circular arcs of the circular end surfaces 251 and the radian of circular arcs of the circular recesses may be equal or unequal. The circular end surfaces 251 are engaged with the circular recesses of the counterweights 23 so as to horizontally position the counterweights 23. The positioning rod 25 is rotated to drive the two circular end surfaces 251 to depart from the circular recesses, so that the lateral retaining of the positioning rod 25 on the counterweights 23 can be released, and hence the counterweights 23 may be added or reduced so as to increase or reduce the self-weight of the drop hammer device 2.

Before disassembling of the counterweight 23, the compression nut 242 on the top of the counterweight 23 must be released by a wrench. Then the positioning block 24 on the top of the hammer block 20 is removed, and the positioning rod 25 is rotated, so that the counterweight 23 can be removed.

As shown in FIG. 9, at a position where the counterweights 23 contact the positioning column 281, circular recesses are also formed to engage with the positioning columns 281 and 282. The two groups of counterweights 23 in the middle may be removed to increase or reduce the self-weight of the drop hammer device 2. But the two groups of counterweights 230 on both sides cannot be added or reduced if the positioning columns 281 and 282 are not removed. Therefore, the positioning columns 281 and 282 may be also removable like the positioning rod 25, so as to, as a selectable way, increase the number of the counterweights for increasing the self-weight of the drop hammer device 2.

The lower hoisting ring 21 is disposed on the upper surface of the upper hammer block 201 and has two end surfaces 210 and two side surfaces 212. The two side surfaces 212 are provided with hoisting hook recesses 213 which are configured to engage with hoisting hooks 423 of the lifting device. A central position of the lower hoisting ring 21 is provided with a central through hole 211 for the sample 6 to pass through. Guide sliding sleeves 22 for the guide columns 12 to pass through are symmetrically disposed on both sides of the central through hole 211.

The drop hammer device 2 is the most important working part in the dynamics performance testing system provided by the present disclosure, and must bear a huge impact, bending force and vibration during impacting the sample 6. The weight of the drop hammer device 2 is adjusted by the change of the number of the counterweights 23.

3. Lifting Device

The lifting device is configured to lift the drop hammer device 2 at the bottom of the vertical frame 1 to a predetermined height for test. For safety reason, the drop hammer device 2 is disposed at the bottom of the vertical frame 1 when not used.

As shown in FIGS. 1 to 4, the lifting device mainly includes a lifting frame 41, a hoisting hook assembly 42, a pulley block 43, a wire rope and a lifting motor 40, etc.

The lifting motor 40 comprises a variable-frequency cycloidal pin gear speed reducer. The motor can achieve the function of stepless variation under the control of a control system, so that the lifting speed of the drop hammer device is infinitely adjustable, and hence the testing efficiency can be improved. The motor adopts an integral speed reducer formed by a motor and a speed reducer. The speed reducer comprises a cycloidal pin gear speed reducer and has at least one of the advantages of small volume, high working efficiency, large output torque and the like.

Figure 3:
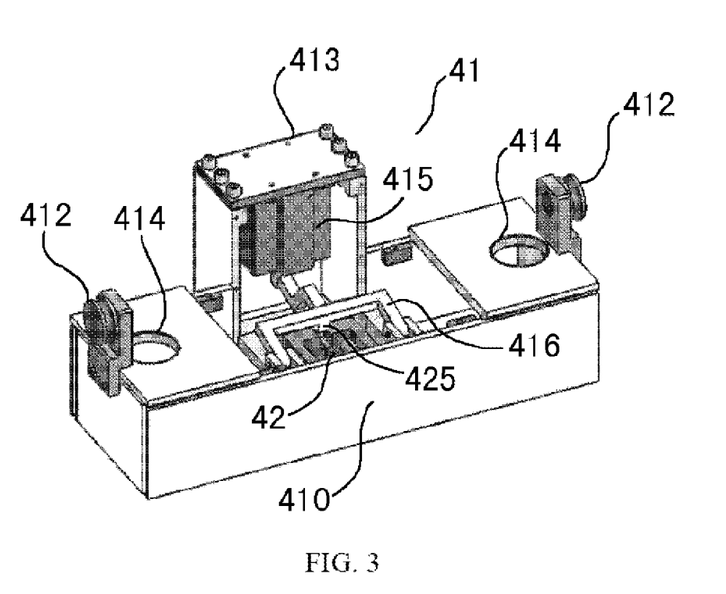
FIG. 3 is a schematic diagram of a lifting frame of a dynamics performance testing system provided by an embodiment of the present disclosure.

The hoisting hooks 423 of the lifting device are disposed in the lifting frame 41. Since the lifting frame 41 must move up and down in the vertical frame 1, it may also be referred to as a movable beam. As shown in FIG. 3, the lifting frame 41 includes a transverse frame 410 and a longitudinal frame 413 connected to a rear end of the transverse frame 410.

As shown in FIG. 3, the transverse frame 410 may be formed by welding steel plates. The hoisting hook assembly 42 including the hoisting hooks 423 is disposed in the transverse frame 410. Clamping hubs 412 are disposed at both ends of the transverse frame 410 and configured to fix a lower end of the wire rope through a rope cramp. An upper end of the wire rope passes through the pulley block 43 disposed on the top platform, and is connected to the lifting motor 40 so as to ascend or descend the lifting frame 41. Through holes 414 for the guide columns 12 to pass through are formed in side of the clamping hubs 412.

An electromagnet 415 is disposed in the longitudinal frame 413 and configured to control the hoisting hook assembly 42 to lock or release the drop hammer device 2. A rotating arm 416 is hinged on both sides of the hoisting hook assembly 42 and is, for instance, Y-shaped. A lock core 425 is connected to the rotating arm 416. When the electromagnet 415 is turned on, the electromagnet 415 drives the rotating arm 416 to rotate, so as to drive the lock core 415 to depart from the hoisting hook assembly 42. When the electromagnet 415 is turned off, the rotating arm 416 falls, so as to drive the lock core 425 to return back to the hoisting hook assembly 42 and hence lock the drop hammer device 2.

Figure 4:
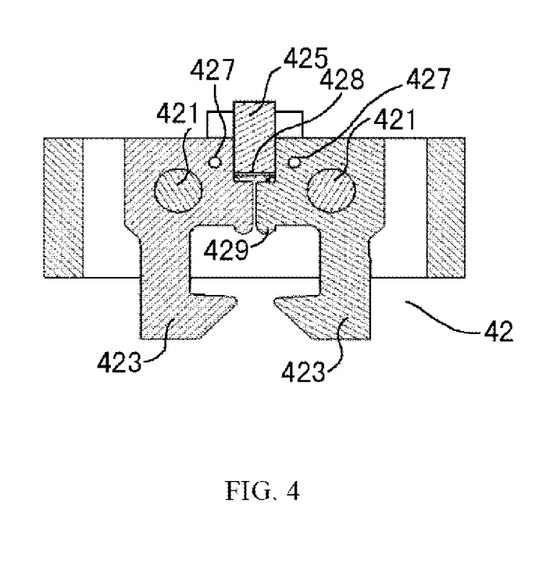
FIG. 4 is a schematic diagram of a hoisting hook assembly of a dynamics performance testing system provided by an embodiment of the present disclosure.

As shown in FIG. 4, the hoisting hook assembly 42 is an important component and includes a lock core 425, a hoisting hook 423, a rotating shaft 421, an offsetting spring 428, a guide portion 429 and the like. There are two groups of hoisting hooks 423 and every group includes two hoisting hooks 423. The two groups of hoisting hooks 423 are arranged opposite to each other; and each group of hoisting hooks 423 share a common rotating shaft 421 in order to rotate in an opposite direction with respect to the other group of hoisting hooks 423.

Step portions are disposed on inner upper edges of the hoisting hooks 423, so that the lock core 425 can be accommodated between two step portions. As shown in FIG. 4 illustrating a locking state of the hoisting hooks 423, when the lock core 425 is disposed between the two step portions, the rotation of the hoisting hooks 423 can be limited, thus the drop hammer device 2 can be prevented from being accidentally released from the hoisting hooks 423. In this state, there is a relative small gap between opposite faces of the two hoisting hooks 423. In order to avoid interference motion between the opposite faces of the two hoisting hooks, the gap can be widened, or the rotating shaft 421 may be disposed above upper ends of the opposite faces.

The offsetting spring 428 is connected between the hoisting hooks 423. The two ends of the offsetting spring 428 are connected to connecting columns 427 disposed on upper portions of the two hoisting hooks 423, respectively. The offsetting spring 428 is configured to drive the two groups of hoisting hooks 423 to rotate in the opposite direction after the lock core 425 is disengaged from the hoisting hook assembly 42, so as to release the drop hammer device 2.

The semicircular guide portions 429 are disposed on inner lower edges of the hoisting hooks 423. When the lifting frame 41 approaches down to the drop hammer device 42, the two hoisting hooks 423 are stretched, and the offsetting spring 428 is in a shrinkage state. Meanwhile the lower hoisting ring 21 passes through bottom ends of the two hoisting hooks 423 and approaches to the guide portions 429 until the lower hoisting ring 21 makes contact with the guide portions 429. Under the acting force of the lower hoisting ring 21, the hoisting hooks 423 are driven to overcome the counterforce of the offsetting spring 428 and rotate in the opposite direction so as to be engaged with the hoisting hook recesses 213 on both sides of the central through hole 211 of the lower hoisting ring 21, while the lock core 45 is clamped between the two step portions to perform locking.

The lifting motor 40 is disposed at the bottom of the vertical frame 1. The lifting motor 40 and the vertical frame 1 (mainly the console 13 thereof) are separately and independently mounted, so that the influence of the vibration of the vertical frame 1 on the lifting motor 40 can be greatly reduced, and hence the installation and the maintenance can be conveniently achieved.

4. Clamping Device

The clamping device 3 is disposed on the top of the vertical frame 1 and configured to vertically clamp the top of the sample 6.

Figure 5:
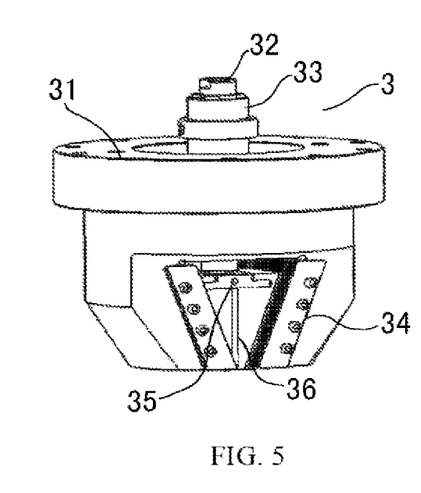
FIG. 5 is a schematic perspective view of a clamp assembly of a dynamics performance testing system provided by an embodiment of the present disclosure.
Figure 6:
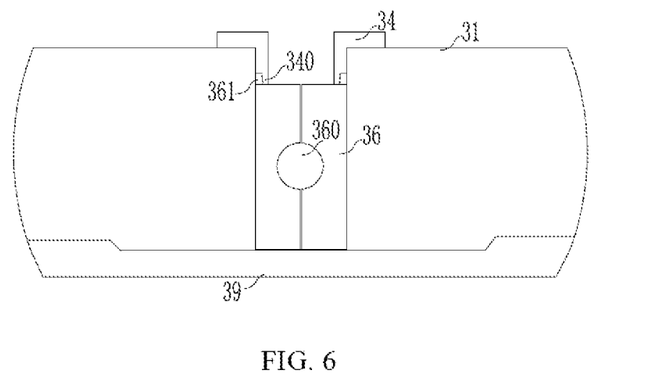
FIG. 6 is a schematic bottom view of the clamp assembly of a dynamics performance testing system provided by an embodiment of the present disclosure.
Figure 7:
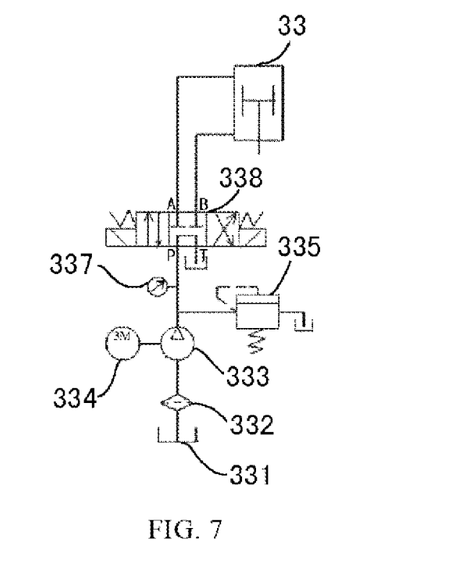
FIG. 7 is a schematic diagram of an oil circuit of FIG. 5.

As shown in FIG. 5, the sample clamping means in the present disclosure comprises hydraulic wedge clamping means. The clamping device 3 includes a clamp cylinder 33, a piston 32, a clamp body 31, two chuck blocks 36, a jaw press plate 34 arranged inclined down, and a push plate 35. As shown in FIGS. 5 and 6, the upward side in FIG. 6 is known as the front side and the downward side is known as the rear side. An opening being in the shape of an isosceles trapezoid is formed on the front of the clamping device. The chuck blocks 36 are in the shape of a right trapezoid, and fixed between the jaw press plate 34 and a back plate 39 in the fore-and-aft direction.

The push plate 35 is connected to a lower end of the piston 32 and driven by the piston 32 to move up and down. A sliding chute cooperated with the push plate 35 is formed on an upper end of each of the two chuck blocks 6 and horizontally slidably connected to the push plate 35. Sides of the two chuck blocks 36 can slide along the obliquely arranged jaw press plate 34.

As shown in FIG. 6, the sample 6 is mounted in a circular hole 360 formed at the bottom of the two chuck blocks 6, and front end portions of the two chuck blocks 6 are provided with convex edges 361 which are engaged with a recess 340 of the jaw press plate 24, so as to achieve the sliding connection between the sides of the two chuck blocks 36 and the jaw press plate 34.

Under the acting force of the piston 33, when the push plate 35 moves up, the push plate 35 will drive the two chuck blocks 36 to oppositely open upwards and outwards, so as to clamp the sample. After the sample is placed, under the acting force of the piston 33, the push plate 35 moves down and can drive the two chuck blocks 36 to oppositely close downwards and inwards, so as to clamp the sample in the circular hole 360.

The chuck blocks 36 are made of high-strength and high-rigidity materials, and provided with helical lines engaged with helical threads of the sample 6, so as to ensure the clamping reliability of the sample 6 in the test process.

The clamping device 3 is equipped with an independent hydraulic source, so as to achieve the manual control of the clamping device 3. FIG. 6 illustrates a schematic diagram of an oil circuit. Members on the oil circuit include an oil tank 331, a coarse oil filter 332, a plunger pump 333, a motor 334, an overflow valve 335, a pressure gauge 337, and an electromagnetic directional valve 338. If an oil pump start button on a handhold control box is pressed, the oil pump is turned on. After a clamping button of the oil cylinder 33 is pressed, the left side of the electromagnetic directional valve 338 is turned on, thus the clamping function of clamping the sample 6 is performed. The clamping button may be a click button. After a test ends, a release button of the oil cylinder 33 is pressed, and the right side of the electromagnetic directional valve 338 is turned on, thus the release function of releasing the sample 6 is performed. If the whole test ends, an oil pump stop button is pressed, and the machine is stopped.

5. Protective Device and Protective Module

In the dynamics performance testing system provided by the present disclosure, as the falling drop hammer device 2 produces a large impact force, noise and potential hazards on staff participating in the test will be produced, and hence the protective work must be particularly done well. The protection of the dynamics performance testing system provided by the present disclosure mainly includes two aspects, namely the protective device in the main frame which focuses on physical protection and mainly reduces the potential hazards by means of isolation and the like, and the protective module in the measure and control system which focuses on safety control, that is, preventing the testing system from producing the potential hazards from the aspect of controlling the test process.

At first, in the dynamics performance testing system provided by the present disclosure, the vertical frame 1 may be disposed in a subsiding environment provided with a protective wall on four faces or three faces respectively, so as to reduce the noise hazard. The console in the measure and control system may be disposed at a relatively high position, for instance, on the top of the protective wall. In order to facilitate the operation of operators, a bridge can be built between two opposing protective walls.

The protective device is not only provided with the above described fence 51 capable of bringing safety control for the work of maintenance staff on the top of the vertical frame 1, but also provided with steel fences 53. The steel fences 53 are as high as two meters, and disposed on the left, front and rear directions of the vertical frame 1, to prevent flaying objects from injuring the people. Moreover, the protective device is also provided with four energy buffers 52 disposed on the console 13. The buffers 52 have the function of buffering and elastically bearing the falling drop hammer device 2, and can effectively reduce the noise. The buffers 52 are disposed just under the drop hammer device 2 and configured to absorb the remaining impact energy of the drop hammer device 2 after the sample 6 is broken. The operation mode of the protective device is hydraulic damping, and the total energy-absorption capacity may be up to 10,000 joules.

The protective module in the measure and control system in the present disclosure may achieve the following protection:

1) Door-opening electrical outage-protection: when a certain part of the main frame fails or the counterweights 23 are required to be disassembled, the operator has to open a protective door to access the main frame. Once the protective door is in the open state, an electrical control system of the dynamics performance testing system will be in the off state and cannot receive any instruction.

2) Upper-limit protection: in order to prevent the lifting motor 40 from exceeding the lifting travel due to inadvertent operation, and hence avoid the "collision" phenomenon, a travel switch is disposed at the maximum travel. The lifting motor will automatically shut down when the maximum as a limit position is reached.

3) Audible and visible alarm: an audible and visible alarm is disposed on the top of one of the support columns 11. Once the main frame enters the drop hammer ready state, the audible and visible alarm will flash and give an alarm. After the drop hammer device 2 is released, the alarm will shut down automatically.

4) Moreover, a detecting apparatus is disposed aside the lock core 424 of the hoisting hook assembly 42 of the lifting device, and configured to determine whether the hoisting hooks 423 are in place. If the hoisting hooks 423 are not in place, the lifting motor 40 will not rotate towards the lifting direction of the drop hammer device 2.

6. Control Means

A control device of the dynamics performance testing system provided by the present disclosure includes a human-machine interface (HMI), a programmable controller (PLC), a frequency converter of the lifting motor 40, a signal input terminal and a signal output terminal, etc., so as to control the normal operation of the drop hammer test process.

Signals input into the signal input terminal may include drop hammer height selection, secondary impact selection, fence state, drop hammer falling state, hoisting hook state, drop hammer switch state, displacement counter acquired by an encoder and the like. Signals output from the output terminal may include drop hammer ready light signal, drop hammer enable signal, visible alarm, audible alarm, anti-secondary-impact signal, frequency converter operation signal, frequency converter stop signal and the like.

The HMI may be a touch interface. A language selection interface is displayed on the touch interface. A user can select simplified Chinese character interface or ENGLISH interface. Once the interface is selected, the user cannot switch the interface when a power supply is not switched on again. That is, in the case of CHINESE TO ENGLISH (the Chinese interface is converted into the English interface) or ENGLISH TO CHINESE (the English interface is converted into the Chinese interface), the power supply must be cut off and switched on again for selection. Moreover, the HMI is also provided with a "Test" option which is a functional option for checking the secondary impact resistance and checking whether the actions of three electromagnets of the drop hammer are normal. In the case of normal test, the user does not need to enter the test interface. Once entering, the user can leave the test interface.

For instance, following options may be provided when the user selects and enters the CHINESE interface:

Speed: referring to the lifting speed of the drop hammer device 2, selected by the user. The user inputs the speed through a speed preset encoder, and the drop hammer device 2 may be lifted according to the speed required by the user.

Height: referring to the height of a position at which the drop hammer device 2 is disposed, displayed by the measurement of an incremental rotary encoder when the user accurately determines the zero position.

Energy: referring to the impact energy of the drop hammer device 2 calculated according to the height at that moment and the mass of the drop hammer device 2.

Pre-height: required height is inputted through the touch interface: the system can automatically pass to the height; and meanwhile the user can finely adjust the position by click.

Weight: referring to the mass of the counterweights selected by the user, added on the basis of the mass of a base hammer. The number of the counterweights can be increased or reduced.

7. Sensing Means

The sensing means includes at least a force sensor disposed on the tray and configured to sense real-time impact data to the tray when the drop hammer device falls vertically.

In the dynamics performance testing system provided by the embodiment, the force sensor may be a YFF-2 impact force sensor. The sensing means may also include a KS60 displacement sensor, a strain foil taken as a stain sensor, a DLF-4 multifunctional charge amplifier, an INV3018A data acquisition instrument taken as a data acquisition module, etc. Signals acquired by the sensors are all sent to the INV3018A data acquisition instrument and hence transmitted to the control module and the analysis module.

The YFF force sensor may be a piezoelectric quartz crystal sensor composed of two groups of piezoids, a conducting strip, a force plate, a housing and a socket, and is circular in shape. The YFF force sensor has a high resolution and can measure the force variation as small as 0.025N in the case of large initial load.

When an external force to be measured is uniformly applied to a bearing surface of the sensor, charges in direct proportion to the external force are produced on surfaces of the piezoids, received by a conducting strip, connected to the charge amplifier through a connecting wire, and output as proportional voltage signals.

The YFF series sensor is a converter for converting "force" into "charge" by utilization of the longitudinal piezoelectric principle of quartz crystals. The charges produced by the sensor are in direct proportion to the external force to be measured and converted into voltage proportionally by the charge amplifier, and the measured force and the variation thereof are directly read by a display or recording instrument.

In the dynamics performance testing system provided by the present disclosure, the YFF force sensor is disposed on a lower surface of the tray 61. Sensing points thereof may be distributed on the same circumference at intervals of 90 degrees.

8. Analysis Module

Analysis is usually performed by a computer operating data analysis program (DASP V10 engineering edition). Analyzing of data acquired according to the test requirements is performed by the conventional analysis method in the field, and the elongation and the radial deformation of a rod body after impact each time are measured. Then an "impact height-accumulative deformation" test curve, an "impact height-impact resistance" test curve, an "accumulative impact energy-accumulative impact deformation" test curve, and an "impact energy-impact resistance" test curve may be drawn respectively, and the data are outputted by the output module.

9. Output Module

The output of the output module mainly comprises two kinds of outputs: one is the output of the test result, and the other is the output of intermediate test data. The test result may be outputted by display, and the test data are stored into hardware of the computer and may also be outputted by an externally connected display interface. Moreover, the intermediate test data may also be outputted in real time through the computer display and the externally connected display interface.

The main technical data of the dynamics performance testing system provided by the present disclosure may be as follows:

Sample size: 2.5 m×□32; sampler space: 500 mm; maximum impact energy: 15,000 J; the total mass of the hammer block: 1,000 kg; the mass of the basic hammer block: 840 kg; the number of the counterweights: four; the weight of each counterweight: 40 kg; the range of effective use height: 0-1.5 m; the linearity of lifting height: 0.5% (via a rope encoder); lifting speed: 0-3 m/min, stepless; the height of the main frame: about 4.5 m; the height space of the main frame: about 5.5 m; the floor area of the main frame: about 3 m×3.5 m.

The operating procedures of the dynamics performance testing system provided by the present disclosure will be described below:

The preparation work includes the following steps:

(1) mounting the sample and checking whether the clamping portion is engaged with the rod body of the anchor rod;

(2) mounting the force sensor and the displacement sensor at the bottom of the tray (if the strain foil is required to be connected, the strain foil should be adhered to the anchor rod before test);

(3) turning on the main power switch, switching on the circuit, and checking whether the circuit can work properly;

(4) checking whether the force sensor, the displacement sensor and the strain foil can read normally; and (5) checking whether all the control keys can work normally.

The operating procedures in the test process:

(1) switching on the power supply;

(2) turning on the start switch, waiting for a few seconds, allowing the touch interface to display a language selection interface, and allowing the user to select a CHINESE interface or an ENGLISH interface, for instance, select the CHINESE interface.

(3) entering the CHINESE interface;

(4) setting the lifting speed of the drop hammer device, in which the speed should not be set to be too fast at the beginning and is preferably 100 mm/s;

(5) falling the hammer body on a cushion block by manual control until a displacement rope on the instrument is in the limit of retaining the elasticity, and adjusting the position to the zero position:

(6) inputting the required lifting height through the touch interface when the user accurately determines the zero position, allowing the hammer body to automatically arrive at the height, and meanwhile allowing the user to finely adjust the position by click;

(7) clicking "the drop hammer to be ready after the hammer body" arrives at the predetermined height, giving an alarm at this moment, clicking a red button on the console, and allowing the drop hammer device 2 to fall freely; and (8) clicking "automatically removing the drop hammer device" after the impact test is completed.

The technical proposal has been disclosed above with reference to the preferred embodiments. It should be understood by those skilled in the art that variations and modifications made without departing from the scope and spirit of the present disclosure disclosed by the appended claims of the present disclosure all fall within the scope of protection of the appended claims of the present disclosure.

The invention claimed is:

1. A dynamics performance testing system, for use in testing a dynamics performances of an anchor rod or an anchor rope, wherein the dynamics performance testing system comprises a main frame and a measure and control device;

wherein the main frame includes:
 a vertical frame;
 a clamping device disposed on the top of the vertical frame and configured to vertically clamp the top of a sample which includes a sample body and a tray at the bottom of the sample body;
 a drop hammer device configured to fall vertically from a predetermined height of the vertical frame to impact the tray;
 a lifting device configured to lift the drop hammer device at the bottom of the vertical frame to the predetermined height; and
 a protective device for physical protection and isolation to reduce the noise and the hazards on the human body; and
wherein the measure and control device is configured to control parameter selection and a lifting and falling of the drop hammer device in a drop hammer test process, sense real-time impact data to the tray through a force sensor when the drop hammer device falls vertically, analyze the real-time impact data received from the sensing means, and form and output a test result.

2. The dynamics performance testing system according to claim 1, wherein the drop hammer device is provided with a central through hole for the sample body to pass through.

3. The dynamics performance testing system according to claim 2, wherein the vertical frame includes four support columns, two guide columns, a fixed beam disposed on the top of the support columns, a console disposed at the bottom of the support columns, and a top platform surrounded by fences and disposed on the top of the fixed beam; and the drop hammer device is provided with a pair of guide sliding sleeves for the guide columns to pass through, arranged on both sides of the central through hole and in parallel to the central through hole.

4. The dynamics performance testing system according to claim 3, wherein the force sensor is a piezoelectric force sensor.

5. The dynamics performance testing system according to claim 2, wherein the force sensor is a piezoelectric force sensor.

6. The dynamics performance testing system according to claim 2, wherein protective walls are disposed on the periphery of the vertical frame; and a hydraulic damper having a function of buffering the falling motion of the drop hammer device is disposed at the bottom of the vertical frame.

7. The dynamics performance testing system according to claim 2, wherein the clamping device comprises wedge clamping means; and chuck blocks of the clamping device are provided with helical lines corresponding to helical threads of the sample.

8. The dynamics performance testing system according to claim 7, wherein sensing points on the force sensor are distributed on the same circumference at intervals of 90 degrees.

9. The dynamics performance testing system according to claim 8, wherein the lifting device is configured to lift the drop hammer device through a lifting motor which is a variable-frequency cycloidal pin gear speed reducer.

10. The dynamics performance testing system according to claim 1, wherein the drop hammer device includes counterweights capable of increasing or reducing the self-weight of the drop hammer device.

11. The dynamics performance testing system according to claim 10, wherein the drop hammer device includes an upper hammer block, a lower hammer block, a plurality of groups of counterweights, a lower hoisting ring disposed on an upper surface of the upper hammer block, and two connecting hammer blocks for connecting the upper hammer block and the lower hammer block; the counterweights are disposed between the two connecting hammer blocks; the lower hoisting ring has two end surfaces and two side surfaces; the two side surfaces are provided with hoisting hook recesses which are configured to engage with hoisting hooks of the lifting device; and the plurality of groups of counterweights are subjected to horizontal position by a positioning rod and a positioning column.

12. The dynamics performance testing system according to claim 11, wherein the positioning rod is rotatably disposed on an upper surface of the lower hammer block;
the top of the positioning rod is in the shape of a right square prism, passes through the upper hammer block, and abuts against an orthogonal recessed surface of a positioning block disposed on an upper surface of the upper hammer block so as to limit the rotation of the positioning rod;
the positioning block abuts against an end surface of the lower hoisting ring and is provided with a slotted hole; a compression nut passes through the slotted hole so as to fix the positioning block on the upper surface of the upper hammer block;
the positioning rod disposed between the upper hammer block and the lower hammer block has two parallel side surfaces and two circular end surfaces; the two circular end surfaces are engaged with circular recesses on the counterweights so as to horizontally position the counterweights; and
the number of the counterweights is increased by rotating the positioning rod to drive the two circular end surfaces to depart from the circular recesses.

13. The dynamics performance testing system according to claim 11, wherein the hoisting hooks of the lifting device are disposed in a lifting frame including a transverse frame and a longitudinal frame connected to a rear end of the transverse frame;
a hoisting hook assembly is disposed in the transverse frame and includes the hoisting hooks; a clamping hub fixedly connected to one end of a wire rope is respectively disposed at both ends of the transverse frame; the other end of the wire rope passes through a pulley block disposed on the top platform and is hence connected to the lifting motor disposed at the bottom of the vertical frame; through holes for the guide columns to pass through are formed inside of the clamping hubs;
an electromagnet is disposed in the longitudinal frame; a rotating arm is hinged on both sides of the hoisting hook assembly; a lock core is connected to the rotating arm; when the electromagnet is turned on, the electromagnet drives the rotating arm to rotate so as to drive the lock core to depart from the hoisting hook assembly; and when the electromagnet is turned off, the rotating arm falls down so as to drive the lock core to return back to the hoisting hook assembly and hence lock the drop hammer device.

14. The dynamics performance testing system according to claim 13, wherein the hoisting hook assembly includes two groups of hoisting hooks arranged opposite to each other; each group of hoisting hooks share a common rotating shaft so as to rotate in the opposite direction with the other group of hoisting hooks;
step portions are disposed on inner upper edges of the hoisting hooks, so that the lock core is accommodated between two step portions;
an offsetting spring is connected between the two groups of hoisting hooks and configured to drive the two groups of hoisting hooks to rotate in the opposite direction when the lock core is disengaged from the hoisting hook assembly, so as to release the drop hammer device; and
semicircular guide portions are disposed on inner lower edges of the hoisting hooks to drive the hoisting hooks to rotate in the opposite direction under the acting force of the lower hoisting ring, so that the hoisting hooks can lock the drop hammer device.

15. The dynamics performance testing system according to claim 11, wherein the clamping device includes a clamp cylinder, a piston, a clamp body, two chuck blocks, a jaw press plate arranged by being inclined down, and a push plate; the push plate is connected to an end of the piston and is driven by the piston to move up and down; upper ends of the two chuck blocks are horizontally slidably connected to the bottom of the push plate; and sides of the two chuck blocks are slidably connected to the jaw press plate.

16. The dynamics performance testing system according to claim 1, wherein the control device switches the control state to the drop hammer ready state and sends a warning signal when detecting that the drop hammer device has reached the predetermined height.

* * * * *